(12) United States Patent
Youngs et al.

(10) Patent No.: US 8,092,691 B2
(45) Date of Patent: Jan. 10, 2012

(54) METHOD AND APPARATUS FOR SEPARATING PARTICLES FROM A LIQUID

(75) Inventors: Ross O. Youngs, Dublin, OH (US); James Robert Cook, Dublin, OH (US)

(73) Assignee: Univenture, Inc., Marysville, OH (US)

( * ) Notice: Subject to any disclaimer, the term of this patent is extended or adjusted under 35 U.S.C. 154(b) by 123 days.

(21) Appl. No.: 12/720,389

(22) Filed: Mar. 9, 2010

(65) Prior Publication Data
US 2010/0224574 A1 Sep. 9, 2010

Related U.S. Application Data

(60) Provisional application No. 61/158,625, filed on Mar. 9, 2009.

(51) Int. Cl.
*B01D 33/04* (2006.01)
*B01D 33/44* (2006.01)
*B01D 33/72* (2006.01)

(52) U.S. Cl. .......... 210/783; 210/400; 210/401; 426/61; 435/243; 435/410; 435/261; 435/257.1; 44/307; 47/1.4

(58) Field of Classification Search .................. None
See application file for complete search history.

(56) References Cited

U.S. PATENT DOCUMENTS

| | | |
|---|---|---|
| 1,892,681 A | 7/1930 | Rankin |
| 1,975,708 A | 10/1934 | Bleibler |
| 2,318,368 A | 4/1939 | Broughton |
| 2,303,123 A | 5/1940 | Johannessen |
| 2,207,278 A | 7/1940 | Albrecht |
| 2,403,021 A | 4/1942 | Peterson et al. |
| 2,714,839 A | 8/1955 | Mazer |
| 2,829,773 A | 4/1958 | Saddington |
| 2,963,160 A | 12/1960 | Wennberg |
| 3,118,748 A | 1/1964 | Delfs |
| 3,138,088 A | 6/1964 | Foth |
| 3,161,522 A * | 12/1964 | Compton .................. 426/436 |
| 3,224,143 A * | 12/1965 | Tew et al. .................. 435/168 |
| 3,352,424 A | 11/1967 | Guebert et al. |
| 3,375,932 A | 4/1968 | Ishigaki |
| 3,405,453 A | 10/1968 | Ries |
| 3,426,908 A | 2/1969 | Davis et al. |
| 3,431,200 A | 3/1969 | Davis et al. |

(Continued)

FOREIGN PATENT DOCUMENTS
EP 0481139 A1 4/1992
(Continued)

OTHER PUBLICATIONS

International Searching Authority, International Search Report and Written Opinion in corresponding Application No. PCT/US2010/026681, mailed May 18, 2010, (13 pages).

*Primary Examiner* — Robert James Popovics
(74) *Attorney, Agent, or Firm* — Wood, Herron & Evans, LLP

(57) ABSTRACT

A method and device for separating particles from a liquid having particles therein, using a filter sized to permit the liquid to flow through pores, while retaining a substantial portion of the particles on the filter, with an absorbent layer contacting the back of the filter to facilitate liquid movement away from the particles.

3 Claims, 4 Drawing Sheets

U.S. PATENT DOCUMENTS

| | | | |
|---|---|---|---|
| 3,459,122 A | 8/1969 | Pastoors et al. | |
| 3,462,360 A * | 8/1969 | McKinney | 210/602 |
| 3,479,281 A * | 11/1969 | Burgaud et al. | 210/703 |
| 3,525,160 A | 8/1970 | Dokoupil et al. | |
| 3,565,797 A * | 2/1971 | Gresham | 210/602 |
| 3,613,564 A * | 10/1971 | Adamski et al. | 100/118 |
| 3,645,040 A * | 2/1972 | Ort | 47/1.4 |
| 3,699,881 A * | 10/1972 | Levin et al. | 100/118 |
| 3,707,230 A | 12/1972 | Davidson | |
| 3,768,200 A * | 10/1973 | Klock | 47/1.4 |
| 3,774,760 A | 11/1973 | Beristain et al. | |
| 3,780,471 A * | 12/1973 | Ort | 47/1.4 |
| 3,796,317 A * | 3/1974 | Lippert et al. | 210/386 |
| 3,836,681 A | 9/1974 | Dodd | |
| 3,854,220 A | 12/1974 | Yamaguchi | |
| 3,863,559 A | 2/1975 | Pierce | |
| 3,875,052 A * | 4/1975 | Lonchamp et al. | 210/637 |
| 3,960,732 A | 6/1976 | Lippert et al. | |
| 3,973,329 A | 8/1976 | Feess | |
| 4,185,680 A | 1/1980 | Lawson | |
| 4,192,743 A * | 3/1980 | Bastgen et al. | 210/712 |
| 4,252,901 A | 2/1981 | Fischer et al. | |
| 4,253,271 A * | 3/1981 | Raymond | 47/1.4 |
| 4,280,658 A | 7/1981 | Ehrrich | |
| 4,341,038 A * | 7/1982 | Bloch et al. | 47/1.4 |
| 4,481,118 A | 11/1984 | Heissenberger et al. | |
| 4,554,390 A * | 11/1985 | Curtain et al. | 568/870 |
| 4,619,194 A | 10/1986 | Pierce | |
| 4,680,314 A * | 7/1987 | Nonomura | 514/725 |
| 4,729,836 A | 3/1988 | Ickinger et al. | |
| 4,851,339 A * | 7/1989 | Hills | 435/67 |
| 4,857,193 A | 8/1989 | Clements et al. | |
| 4,929,353 A | 5/1990 | Harris | |
| 4,958,460 A * | 9/1990 | Nielson et al. | 47/1.4 |
| 5,269,945 A | 12/1993 | Holmberg | |
| 5,306,623 A | 4/1994 | Kiser et al. | |
| 5,445,746 A | 8/1995 | Lee | |
| 5,518,606 A | 5/1996 | Mohle | |
| 5,558,779 A * | 9/1996 | Eriksson | 210/774 |
| 5,573,667 A | 11/1996 | Benesi | |
| 5,701,682 A | 12/1997 | Chuang et al. | |
| 5,804,069 A * | 9/1998 | Eriksson | 210/248 |
| 5,951,875 A * | 9/1999 | Kanel et al. | 210/703 |
| 5,961,796 A | 10/1999 | Hitchens et al. | |
| 6,524,486 B2 * | 2/2003 | Borodyanski et al. | 210/703 |
| 6,893,562 B2 * | 5/2005 | Busnach et al. | 210/248 |
| 6,989,099 B2 * | 1/2006 | Busnach et al. | 210/650 |
| 7,112,281 B2 * | 9/2006 | Busnach et al. | 210/650 |
| 7,125,493 B2 | 10/2006 | Wang et al. | |
| 7,536,827 B2 * | 5/2009 | Busch et al. | 47/62 R |
| 2003/0132162 A1 * | 7/2003 | Busnach et al. | 210/650 |
| 2005/0145581 A1 * | 7/2005 | Busnach et al. | 210/790 |
| 2007/0048859 A1 | 3/2007 | Sears | |
| 2008/0009055 A1 * | 1/2008 | Lewnard | 435/262 |
| 2008/0052987 A1 * | 3/2008 | Busch et al. | 47/62 R |
| 2008/0311649 A1 * | 12/2008 | Cloud et al. | 435/292.1 |
| 2009/0159010 A1 * | 6/2009 | Spartz | 119/200 |
| 2009/0203115 A1 * | 8/2009 | Busch et al. | 435/252.1 |
| 2010/0005857 A1 * | 1/2010 | Zhang et al. | 73/29.02 |
| 2010/0105125 A1 * | 4/2010 | Haley, III | 435/257.1 |
| 2010/0144017 A1 * | 6/2010 | Shepherd | 435/257.1 |
| 2010/0224574 A1 * | 9/2010 | Youngs et al. | 210/783 |
| 2010/0279395 A1 * | 11/2010 | Haley, III | 435/292.1 |
| 2010/0287829 A1 * | 11/2010 | Bussell | 47/1.4 |
| 2010/0314323 A1 * | 12/2010 | Lean et al. | 210/703 |
| 2011/0016773 A1 * | 1/2011 | Nichols et al. | 44/307 |
| 2011/0045556 A1 * | 2/2011 | Das et al. | 435/134 |
| 2011/0107664 A1 * | 5/2011 | Rancis et al. | 47/1.4 |
| 2011/0113682 A1 * | 5/2011 | Ma'Ayan et al. | 47/1.4 |
| 2011/0114556 A1 * | 5/2011 | Donham et al. | 210/612 |
| 2011/0117638 A1 * | 5/2011 | Veres et al. | 435/292.1 |
| 2011/0120944 A1 * | 5/2011 | Ma'Ayan et al. | 210/602 |
| 2011/0143012 A1 * | 6/2011 | Rettenmaier | 426/648 |
| 2011/0201063 A1 * | 8/2011 | Mitropoulos | 435/134 |

FOREIGN PATENT DOCUMENTS

| | | |
|---|---|---|
| EP | 0778908 B1 | 6/1997 |
| WO | 8102528 A1 | 9/1981 |
| WO | 9511075 A1 | 4/1995 |
| WO | 9711767 A1 | 4/1997 |
| WO | 02070817 A1 | 9/2002 |
| WO | 2005010140 A1 | 2/2005 |
| WO | 2005075736 A2 | 8/2005 |

* cited by examiner

METHOD AND APPARATUS FOR SEPARATING PARTICLES FROM A LIQUID

CROSS REFERENCE TO RELATED APPLICATIONS

This application claims the benefit of U.S. Provisional Application Ser. No. 61/158,625, filed on Mar. 9, 2009.

FIELD OF THE INVENTION

The invention generally relates to devices and methods for separating particles from a liquid containing particles therein, and more particularly for separating algae from water.

BACKGROUND OF THE INVENTION

There are thousands of strains of algae, both naturally occurring and genetically modified, known to exist. A significant portion of these strains are known to produce various organic materials which can in turn have commercial utility, such as but not limited to biodiesel, pharmaceutical and nutriceutical applications. The materials produced by algae are sometimes formed within the cellular walls of the algae, but alternatively they may be excreted and available on the outside surface of the algae. In either case, to isolate the materials, it is usually necessary to first separate the algae from the medium in which they grow, which is typically water based. The concentrated algae, also known as an algae paste or cake, may be able to be processed containing amounts of residual water. Or, it may be preferred, or even necessary, to completely dry the algae prior to further processing.

A number of processes have been developed in conjunction with removing or separating algae at various levels of maturity from the growth medium, again typically water based. The processes have included flocculation, sedimentation, flotation, centrifugation, vibratory separation, micro-screening, filter press methods, belt press methods, and methods involving use of a dry bed. Occasionally, more than one method is used in combination. Generally, the above processes can require substantial energy input to effect separation, and the resultant product will still require further drying before processing to isolate the desired organic material can begin.

In addition, practicing several of the above processes can create indirect disadvantages in the overall process of extracting organic material from algae. For example, flocculation, sedimentation, and flotation methods generally require a batch strategy for harvesting algae which requires removing most of the algae from the growth pond or vessel. This step results in substantially less algae in the pond or vessel to carry on the propagation process which negatively affects productivity. Alternatives to the batch strategy exist, such as the use of multiple tanks to create a semi-batch process. But, this alternative also requires more space, capital and time. Also, several of the above processes can damage or destroy individual algae cells resulting from the stresses imposed by the separation process.

SUMMARY OF THE INVENTION

The invention can be generally described as a device for facilitating separation of particulate matter from a liquid containing the particulate matter, such as water. In particular, algae can be separated from carrier fluid, such as water; but other particulate materials can also be separated from a liquid by use of the device. The invention also contemplates a method for effecting such a separation, again in reference not only to algae, but other particulate materials as well. The method effects separation at a relatively low expenditure of energy, and utilizes low differential pressure which minimizes damage to the particles being separated.

The device comprises a filter which is positioned within a frame, with an absorbent layer located in contact with the filter to facilitate removal of liquid such as water. The filter has upper and lower surfaces, and pores which communicate between those surfaces. The pores of the filter are sized so that at least a substantial portion of the particulate matter to be separated cannot penetrate substantially into the pores. In the context of an application involving separating algae from the nutrient water, a mixture of algae in water is applied to the upper surface of the filter. Water begins to separate from the algae, flowing through pores in the filter to the lower surface of the filter. The absorbent layer is placed into contact with the lower surface of the filter, and water contacting the absorbent layer is drawn away from the lower surface of the filter, thereby drawing more water through the pores from above. A dampened absorbent layer more efficiently removes water from the lower surface of the filter than one which is dry. Because sufficient build-up of algae on the upper surface of the filter can limit water flow, the filter optionally is moved relative to the input point of algae and water. In addition, methods for facilitating flotation of the particle to the surface of the liquid-particle mixture will tend to concentrate the particles away from the upper surface of the filter and allow liquid to flow through the pores more easily. Also, because the capacity of the absorbent layer to absorb water is finite, optionally the absorbent layer is moved relative to the location on the filter where water is flowing through the pores. The filter can move relative to the input point for the algae and water, and the absorbent layer can move relative to the filter either in the same direction but at a different rate, or in a different direction relative to the filter. Thus, the filter can move alone, the absorbent layer can move alone, or both can move. As another alternative, the input point for the mixture onto the filter can move relative to the filter, or multiple input points can be used. Compared to conventional centrifuge methods of separating solid and liquid components of a mixture, the method of separating using this device on algae is expected to effect the separation with a substantial energy reduction compared to centrifugal separation, up to a 95% reduction, and to attain a higher solids content in the concentrated product compared to centrifugal separation.

Further, this method uses a relatively low degree of differential pressure to assist in facilitating water movement through the pores. As a result, the particle is neither pushed nor pulled into the pores of the filter, and blinding or blocking of the pore inlets is negligible. In addition, the method imposes low deforming forces on the particle. In the case of separating algae from water, this feature assists in preserving the structural integrity of the algae cells. This aspect of the method contributes to maintaining the contents, typically oil-bearing, of the algae for later processing. And, gentle drying of the algae can then place the algae in a dormant phase which allows for later reanimation under growing conditions.

After a substantial portion of the water is separated from the particle, the particles remaining on the upper surface of the filter can be further reduced in water content by one of a number of techniques, and then removed from the filter for further processing. In the case of algae, one example of further processing is the extraction of organic material from the algae. The filter can be configured on the device as a continuous loop mounted on the frame, and the absorbent loop can also be configured as a continuous loop, or as a plurality of smaller continuous loops so that at least a portion of the absorbent layer makes contact with a portion of the lower surface of the filter in operation. Water absorbed by the absorbent layer can be removed, and the layer reused, by passing the layer between two rolls or similar components which extract the entrained water from the layer. Intermittently, the filter, absorbent layer, or both, may be cleaned to remove any accumulation of particles over time by chemical or physical operations, and thereby open partially or completely clogged pores. Because of the low differential pressures employed in practicing the method, the filter can remain in operation, even continuously, for long periods of time before cleaning or refurbishing is required.

As further described herein, the device and method of separating are primarily discussed in connection with separating algae particles from water or similar growth medium, though the separation of other particles and particle types is envisioned.

DETAILED DESCRIPTION OF THE INVENTION

Figure 1:
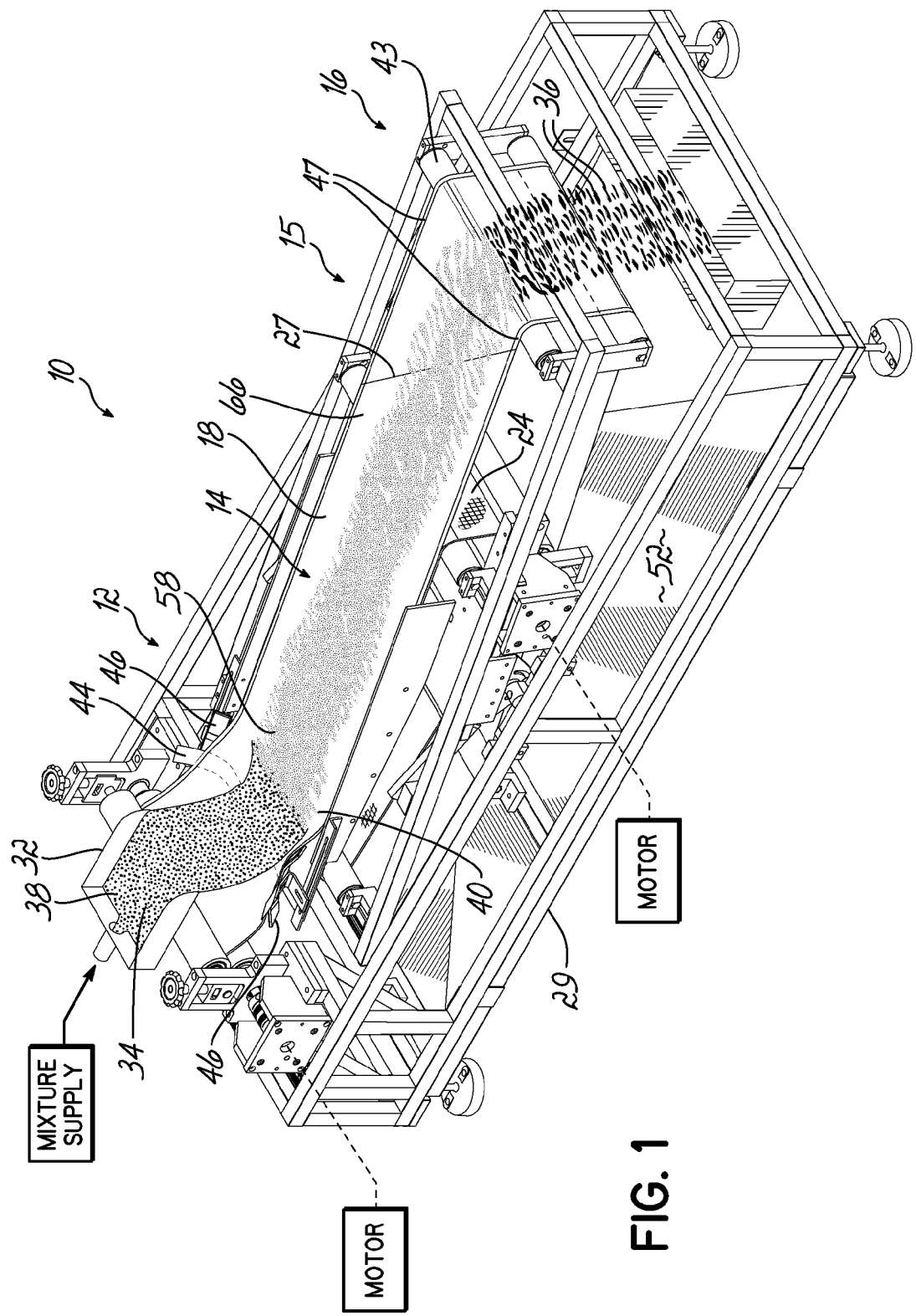
FIG. 1 is a perspective view of a frame configured with a screen and absorbent layer, operating to receive a mixture of algae and water and separate the components.
Figure 2:
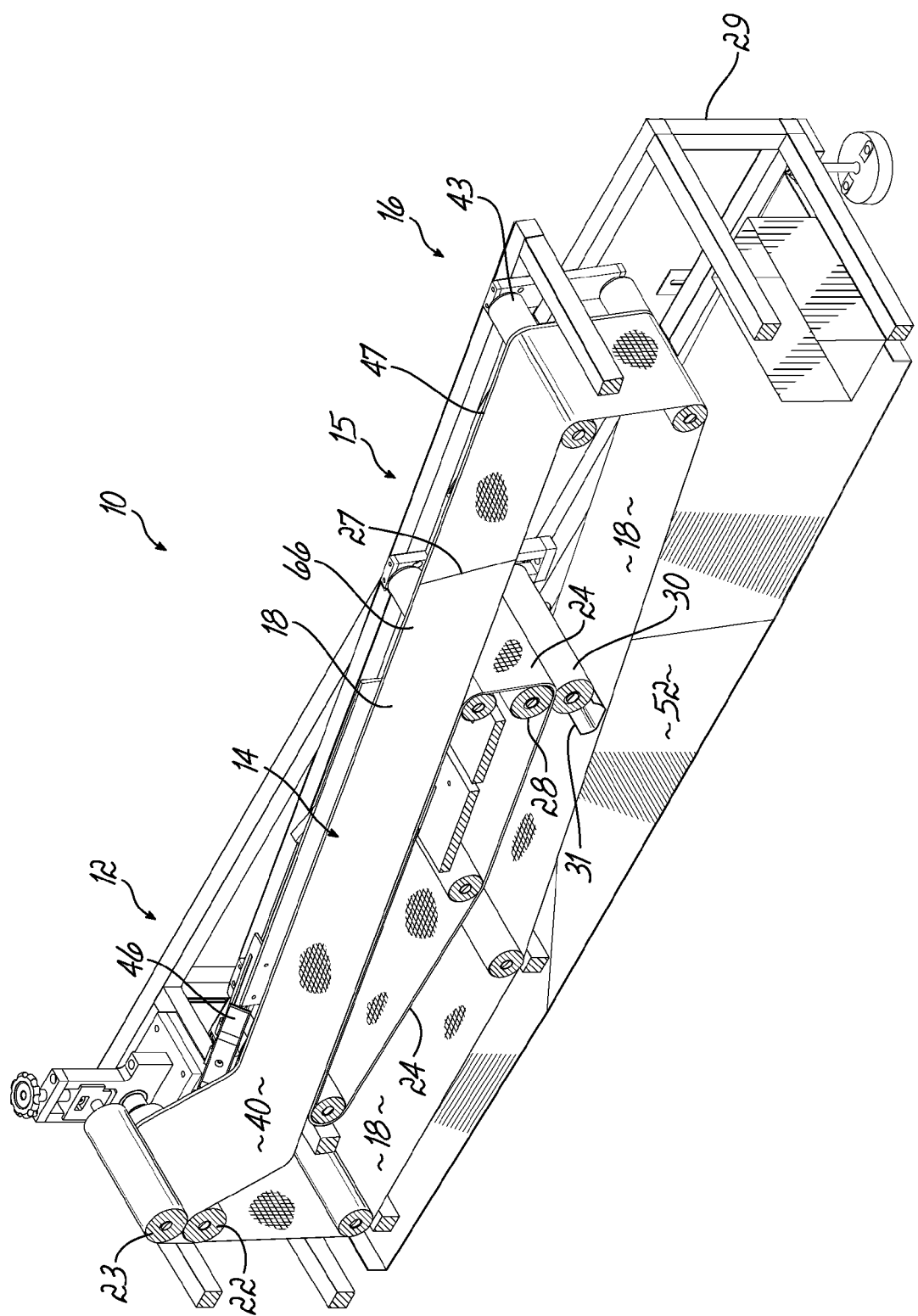
FIG. 2 is a perspective cross-section of the embodiment of FIG. 1, with the algae and water omitted.

The invention is directed to separating particles from a liquid containing particles therein, encompassing a device and a method of processing. The invention utilizes a filter having an upper surface on which liquid containing particles, such as algae in water (an algal mixture), is placed. The filter further includes a lower surface and pores, with at least a portion of the pores extending from the upper surface through to the lower surface. Further, the separation takes place with low expenditure of energy. And, the separation operates at a low differential pressure, which imposes relatively slight stresses to individual particles, minimizing damage to the particles. In the case of separating algae from water, the pores in the filter are sized to allow the liquid to pass through the pores, while keeping algae on the top surface. Some percentage of particles may pass through the pores, and a pass-through amount of up to about 10% to about 15% of the particles is considered acceptable. The particles may partially or completely block some portion of the inlets of the pores, and thus the flow rate of liquid through the pores may decrease with time. However, the low differential pressures employed in practicing the method will generally not cause severe or irreversible blockage of pores. And, agglomeration attributed to the reduction in moisture of the particle cake tends to lift those particles which may have caused some port blockage away from the pore inlets.

Depending on the flow rate of the mixture of particles and water onto the filter prior to separation, the rate of the flow of liquid through the filter may result in formation of a pool of the algal mixture on top of the filter. This pool may form in a depression along the filter surface by the exertion of a downward force from the mixture near the filter's center width, in combination with slack in the filter created by rotation of the rollers conveying the filter toward that portion comprising the pool boundary. The pool is replenished with algal mixture from a source. The mixture can be either continually or intermittently replenished, and can be introduced via a single input point or a multiplicity of points. Thus, for example, the mixture can flow onto the filter and into the pool via a single inlet pipe, or via a manifold which in turn supplies multiple inlet nozzles. Where the filter moves relative to the input source, before the pores of the filter can become clogged from the volume of algae covering the filter, the available filter surface is replenished with fresh filter surface, while the filter with the algae on its top surface is moved out of the pool of retained particles and water, or away from the location where the algal mixture is introduced.

The area or portion of filter that now has algae on it, in the form of a wet paste on its top surface through which water may still be flowing, is brought into contact with an absorbent layer on the lower surface of the filter. The absorbent layer may be moved relative to the location on the filter through which water drains, to expose relatively dry absorbent material to facilitate the absorption of the water flowing around the algae and through the filter pores. Water absorption is facilitated if the absorbent layer is damp, such that some residual water is retained in the layer. After the absorbent layer makes contact with the underside of the filter and removes water from around the algae particles, the algae cake contains far less water than it did before the bottom surface of the filter was brought into contact with the absorbent material. The algae cake's water content can be further lowered if desired by other means, such as by adding heat or introducing an air flow such as with a heating element, a fan, a blower, a light source an acoustic device or a vacuum, which can be introduced either above or below the algae cake.

The algae may be collected from the filter in a variety of ways, for example by bending the filter after sufficient drying so that the cake lifts off the filter surface. Other treatments which facilitate collection of the algae include passing the filter containing algae over a patterned, non-smooth surface roll, or applying a doctor or scraper blade directly to the upper filter surface. Since no substantial physical forces have been applied to the algae because of the low differential pressure at the upper surface relative to the lower surface of the filter, the algae is not driven significantly into the pores of the filter as long as the filter pores are sized properly relative to the effective size of the algae particles, either singly or as agglomerated particles. The low moisture algae cake is thus relatively easy to remove, allowing the filter to be reused. Of course, if the effective size of the algae particles (or a portion of the particles) is smaller than the pore size of the filter, those algae particles which reach the pore are more likely to pass through, and optionally be re-collected below. The absorbent material may also be reused if a portion of the retained water can be repeatedly expelled, such as by passing the material between two pinch rollers or other components capable of expressing liquid from the material such as a compression roller, a vacuum, an air blower, a heater element, and a restrictive plate pair. In one embodiment, the algae cake when dry (i.e., greater than 90% solids) would have a thickness of 25-900 microns ($\mu$). Lesser thicknesses would be expected to result from the process of separating smaller diameter particles relative to those having large diameters.

In one embodiment, the absorbent material is in the form of a continuous loop or belt, with a direction of travel which is countercurrent to that of a continuous loop filter belt. Configured in this way, with passage of the absorbent belt between components to express retained liquid, the device brings relatively low moisture absorbent material into contact with the filter belt retaining the pool of algae mixture and thus having a relatively high water content. This countercurrent travel arrangement thus tends to facilitate the transfer of water from the algae mixture through the filter pores. The structural integrity of the continuous filter belt is improved by creating an edging along the edge borders of the belt. The belt is less prone to distortion by incorporating the edging. Rollers or clips can engage the filter edging to assist in providing cross-web tension, and also to guide the filter belt. The structural integrity of the absorbent belt material is improved by affixing a reinforcing material beneath the absorbent material. Good results were obtained by affixing a fiberglass window screen material as a webbing to the underside of the absorbent material, secured for example by sewing the layers together. With continuous belts, it is important in use to have a seam presenting a low profile appearance so that undue wear at the seam is minimized.

Also, it is contemplated that the pool containing an algae or other particulate mixture can receive a frothing device, such as an air bubble frothing unit, or magnetic or electrical frothing devices (not shown), to concentrate particles such as algae at or near the surface of the pool. More particles at or near the surface of the pool result in comparatively fewer particles at or near the upper surface of the filter, thus allowing comparatively more liquid to flow through the pores without being impeded or blocked by particles. To minimize energy consumption, the efficiency improvement attributable to the flotation unit should be balanced against the increased energy consumption attributed to operating that unit.

The absorbent material in one embodiment is described as a single, continuous loop or belt. Alternatively, the absorbent material may also include one or more absorbent rollers, or multiple continuous belts of shorter length positioned beneath the filter, or combinations of shorter length belts and rollers.

Figure 3:
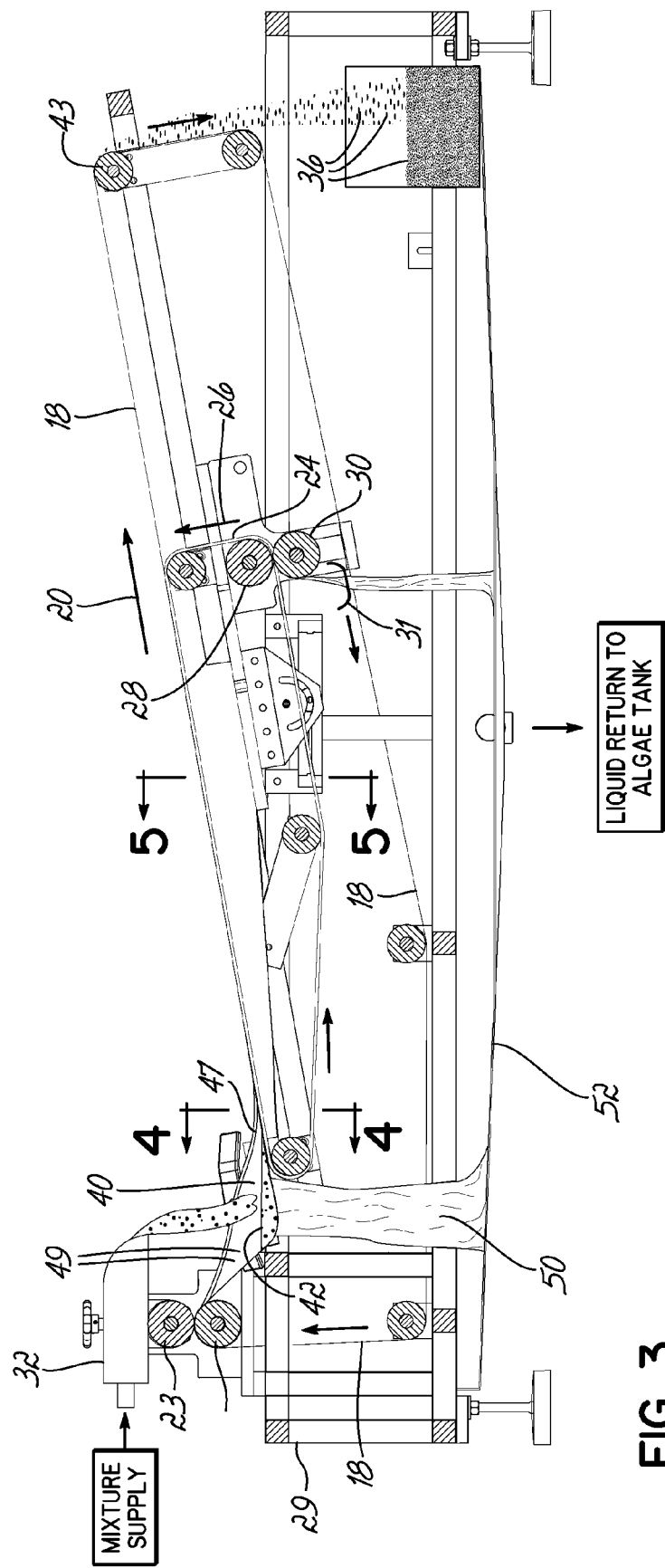
FIG. 3 is an elevational cross-section of the embodiment of FIG. 1.

In an embodiment of the invention illustrated in FIGS. 1-7, the device 10 has a separating section 12, a dewatering section 14, an optional drying section 15, and a collection section 16. In FIG. 3, a continuous loop filter belt 18 travels in a direction shown by arrow 20 driven by a drive roller 22 that is opposite a load roller 23. The filter belt 18 may include a seam 27 having a low profile and/or a structure supporting the filter material. Interior to the continuous loop formed by the filter belt 18 is an absorbent belt 24 contacting the filter belt 18 traveling in the opposite direction as shown by arrow 26. The absorbent belt 24 may also form a continuous loop. The continuous absorbent belt is driven by a drive roller 28. A squeeze roller 30 is opposite the drive roller 28, and applies pressure to squeeze out liquid from the absorbent belt to be caught on a catch tray 31. Variable speed motors drive both the filter belt 18 and the absorbent belt 24 so that the belt speeds and thus the device 10 can be adjusted as needed for a wide variety of input conditions. The motors may also be reversing, which may be beneficial in certain situations, such as maintenance and repair, or to facilitate separation of different types of particles and liquids. The motors may include integral components for measuring energy consumption, or be connected to discrete energy consumption devices to measure the power draw. The various components of the device are affixed to the frame 29.

A mixture input 32, for example a waterfall weir containing the mixture of particles and liquid, is positioned to deposit the mixture, shown as an algal mixture 34 consisting of microalgae 36 and water 38 in the separating section 12. It has been found that, using the *Euglena* strain of algae, a solution of 3 grams of algae per liter of water provides a mixture which has acceptable flow properties for conveying algae and separating it from the water component. A solution of 100 g per liter of water for the *Euglena* strain has an unacceptably high viscosity which interferes with water removal through pores in the filter belt 18. When other strains are used, unacceptably high viscosities can be obtained with concentrations in a range of 60 to 100 g per liter of water. In one embodiment, the concentration of solids (as particles) in liquid can be in the range of 2-3 g/liter. A concentration of 15 g/liter in another embodiment can be applied to a screen, with acceptable separation of liquid. A solution of less than about 0.5 g algae per liter of water generally deposits too little algae on the surface of the filter belt 18 to permit effective separation of an algae cake from the filter belt 18. The upper and lower concentration limits of the algal solution will vary with the algae strain being separated, the maturity (and thus the particle size of the algae) and the presence (or lack thereof) of any exudate or contaminants generated by the algae particles and deposited on the outer surface of individual particles.

It has also been found beneficial to deposit the mixture in an area of the filter belt 18 that has been configured to form a depression in the form of a well 40, to ensure that the mixture does not flow over the edges of the filter belt 18, and that a sufficient amount of mixture has been added to provide a generally uniform coating of material across the width of the filter belt 18. The mixture may form a pool 42 in the well 40, and the weight of the pool 42 and the edges of the filter belt 18 in the separating area are supported by a bottom support 44 and side guides 46. The bottom support 44 may be a curved piece of plastic, and the side guides 46 may be stainless steel, but alternative designs and materials of construction can be used. Further, one or both of the bottom support 44 and the side guides 46 may not be required in an alternate configuration. The presence, absence, or dimension of the pool 42 is controllable by the rate of input of mixture 34, and the respective speeds at which the filter belt 18 and absorbent belt 24 are driven. In one embodiment, the filter belt 18 receives edging 47 to assist in stabilizing the belt, and to seal the fibers.

Figure 4:
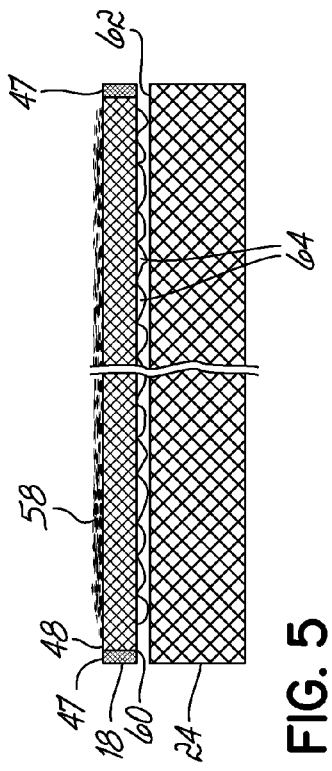
FIG. 4 is a schematic cross-section as indicated in FIG. 3.

In operation, the mixture 34 is deposited on a top surface 48 of the filter belt 18 in the well area 40. As shown in FIG. 1, the mixture supply is introduced via a horizontally oriented pipe. However, alternate introduction components can be used, such as an overhead vertical pipe or an overhead manifold with multiple outlets spanning optionally up to the entire width of the filter belt 18. The filter belt 18 allows liquid such as water to pass through its pores 49 under the force of gravity in a stream 50 (FIG. 3) which is collected in a catch pan 52. The pores are sized such that particles such as algae, of a certain size, either individually or as an agglomerate, are retained on the top surface of the filter belt 18. As the particles such as algae are mixed around in the pool 42 some of the particles settle on the top surface 48 of the filter belt 18 at the bottom of the pool, while other particles continue to be agitated in the mixture. As the filter belt 18 advances, a fresh surface area of filter enters the pool at the upstream end 54 (FIG. 7) while a partly covered area of filter exits the pool at the downstream end 56. As the filter exits the inclined sides of the pool, additional particles settle on the top surface 48. All the particles on the filter form a wet cake 58 having water as shown in FIG. 4. Though not shown, a froth flotation device, such as an aerator or acoustic, magnetic, or electrical concentrating devices, can be used to concentrate particles at or near the surface of the pool 42, and thus away from the top surface of the filter belt 18 to facilitate liquid flow through the pores of the filter belt 18.

As the filter belt 18 with wet cake advances, some water continues to pass through the filter belt 18 pores by gravity. Additionally water passage through the filter pores and away from the algae is facilitated by contacting the absorbent belt 24 to the lower surface 60 of the filter belt 18. In one embodiment, the absorbent belt 24 nearest the mixture supply end of the device 10 will contact the lower surface 60 of the filter belt 18 beneath a portion of the well area 40.

Figure 5:
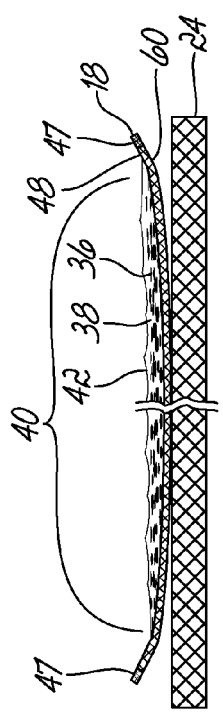
FIG. 5 is an enlarged schematic cross-section as indicated in FIG. 3.

As the filter belt 18 advances the progressively lower moisture content algae cake, the bottom surface 60 of the filter belt 18 contacts and rests upon the top surface 62 of the absorbent belt 24. This absorbent belt 24 in one embodiment travels in the opposite direction of the filter belt 18, and alternatively travels at a different rate from the filter belt 18, in either the co-current or counter-current direction. The absorbent material makes hydraulic contact with the water droplets 64 forming and attempting to drop from the pores 49 of the filter belt 18. FIG. 5 is drawn with a gap, to illustrate the water droplets forming. Typically, however the two belts are actually in contact. The absorbent material wicks the liquid from filter pores, thus allowing the pores in the filter belt 18 to pull or receive liquid from the interstitial spaces around the particles, with the liquid ultimately being drawn into the absorbent material. Maintaining the moving filter belt 18 in contact with the counter-rotating absorbent belt 24 allows the algae cake 58 to increase its solids content as it is exposed to relatively dry absorbent belt material.

As the section of the filter belt 18 having the particle cake breaks contact with the absorbent belt, at 66, it enters an optional drying area 15 that can further reduce moisture levels by any number of means depending on the needs of the process. The drying area may require nothing else be done so that further drying takes place under ambient temperature and humidity conditions. Or, one or more active drying methods may be used such as, for example, air movement, heating, dehumidification, sunlight, or combinations. These methods may be accomplished with a heating element, a fan, a blower, a light source, an acoustic device, and/or a vacuum. In one embodiment the high solids cake peels from the filter belt 18 once a moisture threshold is reached, and the belt speeds and mixture input volumes can be varied so that additional drying becomes unnecessary. The porous structure of the filter belt 18 also allows an active drying method such as air movement or heat to be applied to the particle cake from above the cake, below the cake, or both. Where the particle is algae, at approximately 34% solids and a thickness in the range of about 25 to 900 microns the algae cake will release from the upper surface of the filter belt 18, and begin to form flakes.

Figure 6:
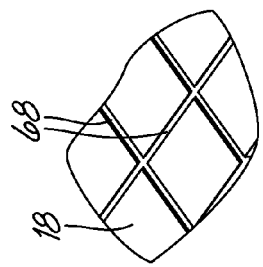
FIG. 6 is a schematic representation of an embodiment of filter material.
Figure 7:
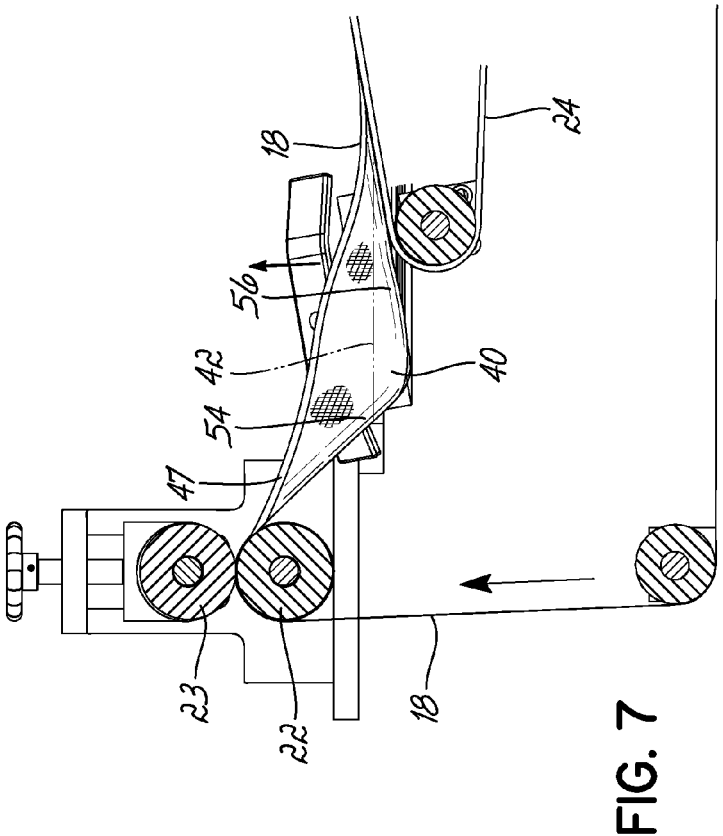
FIG. 7 is a detail schematic cross-section view of a portion of the embodiment of FIG. 1.

At the collection section 16, the flexible filter belt 18 changes direction at an angle of about 90 degrees or greater. The lower moisture algae cake, being less flexible, cracks and falls off the belt to be collected. A variety of other collection enhancement methods may be used as necessary. They include, for example, making a turn sharper than the radius turn illustrated around a roller. This can be done, for example, by passing the filter element over an edge to change direction of travel, instead of the smooth radius roller. Scrapers, vibrators, blowers, augers, brushes, vacuums and the like may also be employed as needed. However, it is desirable to maintain zero or near zero energy use whenever possible. In addition, it is contemplated that filter belts may be used that have intentionally blocked off pores 68 such as illustrated in FIG. 6, which prevent forming a uniform cake. By working with an intentionally segmented cake rather than one large continuous one, the drying and peeling-up properties may be influenced, so that cake is more easily separated from the filter belt. This is possible because no forces, such as pressure differential (by vacuum drawing effects, or air pressure pushing effects), or rollers or the like have been used that would contribute to drive the algae cells 36 into the pores 49 of the filter belt 18.

The device 10 includes one D.C. drive motor for causing movement of the flexible filter belt 18 relative to the frame 29 and a separate D.C. drive motor for causing movement of the absorbent material at a same or different rate of speed. In one embodiment the energy utilized for harvesting and dewatering the algae to at least 20% solids, introduced as a dilute mixture in water can be less than 100 watts per kilogram algae dewatered, in another embodiment less than 400 watts per kilogram algae dewatered and in another embodiment less than 700 watts per kilogram algae dewatered when concentrating from a solution of 0.3 g algae/liter solution to at least 200 g/liter. In another embodiment, the energy consumption is about 26 watts per kilogram algae dewatered when dewatering to at least 20% solids.

Example

The following example illustrates the practice of one embodiment of the invention using the device to dewater a particular strain of algae. Other embodiments within the scope of the claims herein will be apparent to one of skill in the art based on the disclosure herein.

The device was configured with a continuous filter made of Polyester monofilament material (product number PES25/20) from SaatiTech, Somers, N.Y., having a pore size (also known as a mesh opening) of 25 microns and an open area of 20%. Thickness of the filter was 52 microns, and the individual thread diameter for preparing the filter material was 27 microns. Beneath the filter belt was a continuous belt of airlaid nonwoven absorbent material, No. NF 52-230 made by Hagulan Vliesstoff GmbH & Co. KG, Fulda, Germany. This belt was made of 80% viscose and 20% polyethylene. The structural integrity of the absorbent belt was increased by sewing a webbing of a fiberglass window screen material to the underside. Both the continuous filter and continuous absorbent belts were seamed to minimize thickness variations and thereby present smooth surfaces relative to each other and the contacting components on the frame. The filter belt moved at a speed of 20.3 cm per minute (8 inches/min.) driven by a DC Motor, to which was connected a Kill-a-watt wattmeter for measuring power draw.

An algae mixture made up of *Chlorella vulgaris* having an average (agglomerated) particle size of 10-40 microns (individual cell sizes ranging from about 2 to about 10 microns), at a concentration of 0.8 g/liter water, was poured into a pool defined by the moving filter belt, at a rate of 1.3 L/min. The absorbent material was moving countercurrent to the filter belt, at a speed of 15.2 cm per minute (6 inches/min.) driven by a DC Motor, to which was also connected a Kill-a-watt wattmeter.

Algae cake exiting the pool had an approximate solids content of about 10%. Within about 15 cm travel of the cake on the filter belt with countercurrent travel by the absorbent belt 24 beneath, the solids content increased to about 16%. Over the remaining 41 cm of the filter belt 18 located above absorbent belt 24, the solids content increased further, to about 18% solids by weight. At the end of the filter belt prior to the cake removal roller 43 the solids content was about 25% solids. Depending on the length of the filter belt and the ambient environmental conditions, further drying can occur without active drying measures being taken. Elapsed time from initial introduction of the algae mixture to removal of a cake having at least about 25% solids was 8 minutes. Energy expenditure for the D.C. motors used to rotate the rollers driving the filter 18 belt and absorbent belt 24 was 17 watts. The weight of algae cake of at least 20% solids produced in the steady state mode per unit time was 3.7 g/min. Thus, 0.077 watt hours (277.2 joules) of energy was expended to produce one gram of algae cake having a 20% solids content. No other energy was expended to reach the solids content for the cake. The ambient temperature in the room was approximately 72° F. with a relative humidity of approximately 50%.

It can be appreciated that different strains of algae will have different particle diameters at maturity. In addition, based on the strain, and maturity of the algae, there may be a greater or lesser tendency for individual algae particles to agglomerate, thus increasing the effective size of the unit to be filtered. Also, the shape of the particle may vary with the strain being used. Thus, the appropriate filter screen material may have different pore sizes to effectively separate the particles from water. Also, the flow rates of the mixture may be varied to optimize particle recovery, and the water absorbing capacity of the absorbent material may need to be appropriately modified. Thus, it is expected that ranges of algae strains, filter screen pore sizes, and absorbance capacities can be utilized as desired. For further comparative information relative to the evaluation and drying characterization for various algae strains, see Table 1 below. The separation conditions were generally the same as those set out above in the Example.

impeded, hampering the separation. It is generally acceptable to have up to about 10% to 15% of the particles passing through the filter belt. Thus, the filter belt mesh opening can be greater than the particle size, though not substantially so. Thus, for example, a mesh opening of 25 microns will effectively separate particles with an average size of about 20 microns, with an acceptable amount of pass through particles. Ranges of filter material for use with the device can span from at least a 7 micron mesh opening up to a 700 micron opening, with an open area of 2% up to 68%, respectively. In selecting the filter material, in one embodiment the portion of the material closest to the mixture has the highest hydrophobicity, with the material then becoming more hydrophilic as it extends away from the mixture. Coatings, such as those based on silicone or fluorinated polymers, can be used to increase hydrophobicity.

Because of the low level of damage to individual algae particles in the separation process, the filter belt 18 can run for extended times without need to clean, replace or refurbish the material. In the format set out in the Example, the filter belt 18 was operated for one week before being taken off-line, soaked in a weak bleach solution for 20 minutes, and returned to operation.

The absorbent material used for the absorbent belt was a needle felt floor cloth (NF 52-230 S) having a weight of 221 g/m$^2$ (grams per square meter), a thickness of (for a 10 oz.) 2.2

TABLE 1

| | Algae | | | | |
|---|---|---|---|---|---|
| | Botryococcus braunii | Chlorella vulgaris | Euglena gracilis | Nannochloropsis salina | Pond Water Marysville, OH |
| Size Range (um) | 15-35 | 2-10 | 15-40 | 0.5-2 | 0.5-40 |
| Density (g/L) | 2 | 2.8 | 3.1 | 40.2 | 1 |
| Algae Energy Content (Watt-hrs/gram Algae) | 7.2 | 5.2 | 5.6 | 6.8 | 4.6 |
| # of Process Runs | 2 | 18 | 12 | 39 | 53 |
| Flow Rate (L/hr) | 456 | 342 | 342 | 60 | 510 |
| Escaped Algae (%)* | 0.5 | 8 | 1 | 35 | 3 |
| Residual Water in Dry Flake (%) | 1.2 | 0.5 | 1.4 | 0.4 | 1.0 |
| Dry Solids Yield (g) | 152 | 147 | 175 | 261.3 | 83 |

*Escaped Algae are the percentage of Algae that transferred with the water through the filter. Generally, the percentage of algae particles which pass through the filter will not exceed 10-15% of the total particles quantity of algae particles.

An example of a filter screen that has been successfully used with the *Chlorella vulgaris* microalgae is a woven polyester filter fabric (PES 25/16) that may be obtained from SaatiTech of Somers, N.Y. The material has a mesh opening of 25 microns, a 16% Open Area, and a thread diameter of 34 microns. Air Permeability is 1,700 l/m$^2$s (liters per square meter per second). The open area is defined as the percentage of pore surface to thread surface for a defined area of the filter fabric. The operative mesh opening is a function of the particle size of the material to be separated from the liquid. A mesh opening substantially larger than the particle size will result in most of the particles passing through the filter belt. If the mesh opening is substantially smaller than the particle size, the pores are more easily blocked or impeded, even with low differential pressure. As a result, liquid movement is mm, a blend of 80% Viscose and 20% polyethylene and an absorption of 1198% or 2.65 liter/m$^2$ (liter per square meter). It is available from Hagulan Vliesstoff GmbH & Co. KG, of Fulda Germany.

Although the above invention has been described in terms of use for the drying of algae, it is also useable for the separation, dewatering, and collection of any other particulate matter from water or another liquid. The properties of such other particulate matter may require adjusting the characteristics of the screen and absorbent layer, so that the screen and absorbent layer are non-reactive with the liquid or the particles. Also, other liquids than water could be used. For example, particulate matter from an ethanol production process were separated from the liquid carrier, as was particulate matter from waste water used in an oil recycling operation.

The embodiment illustrated and described herein has a single absorbent belt traveling within the screen for the purpose of separating the algae from water or other liquid in which it is grown or conveyed. It is also envisioned that other processes can be carried out on the algae while it is on the screen belt, or after it is transferred to another belt. For example, the traveling screen belt may pass under a nozzle that sprays solvent on the algae cake for the purpose of removing oils or other substances present on the exterior of the algae. This solvent would then pass through the screen and be collected. The desirable material, for example a lipid, could then be separated from the solvent and the solvent re-circulated. Also, a second absorbent belt may be brought into contact with the bottom of the filter belt, to assist in further reducing the moisture level of the algae cake before its final collection. It is contemplated that during the process of removing organic material from the outside surface of the algae particles, the algae may be kept alive and undamaged, so that they can be returned to the tank to produce more material on the outside surface. Since algae that produce materials extracellularly often have a slower rate of reproduction, this frequent harvesting of organic material from the outside surface and return would be used to keep production rates at a desired level.

The embodiment illustrated and described herein employed a horizontally oriented belt surface. Variations in orientation are possible. It is also envisioned that a device may be configured having a round disk of filter screen traveling in a first direction around an axis and a disk of absorbent material traveling the opposite direction around a second axis, along with an appropriate way of removing the cake material, for example with a scraper or a vacuum. Similarly, the device may be made in the form of cylinders, for example with the algae being placed on the outside of a cylinder of screen, and an absorbent material on the inside.

While the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of Applicants' general inventive concept.

What is claimed is:

1. A method for separating algae from a mixture containing algae and water, comprising the steps of:
    providing a separation device including:
        a filter including an upper surface at least a portion of which is configured to receive said mixture, a lower surface, and pores extending between the upper and lower surfaces wherein the pores are of a size sufficient to allow water to pass while preventing at least some algae from passing through said filter;
        an absorbent layer including an upper surface and a lower surface, wherein at least a portion of said lower surface of the filter contacts at least a portion of the upper surface of the absorbent layer;
        at least one movement device for effecting relative movement between said filter and said absorbent layer; and
        a frame supporting said filter and said absorbent layer in a manner that allows the filter and absorbent layer to move relative to one another;
    placing a mixture containing algae and water onto said upper surface of said filter;
    allowing water to pass through said filter and be absorbed by said absorbent layer without the application of any external force to said mixture, thereby producing a concentrated algae on said upper surface of the filter;
    effecting relative movement between said filter and said absorbent layer; and
    collecting said concentrated algae from said upper surface of the filter.

2. The method of claim 1 wherein the filter and the absorbent layer are respectively continuous loops moving in a countercurrent direction relative to one another.

3. The method of claim 1 further comprising removing at least a portion of the liquid absorbed into the absorbent layer.

* * * * *